(12) United States Patent
Wollenweber et al.

(10) Patent No.: US 8,131,044 B2
(45) Date of Patent: Mar. 6, 2012

(54) METHOD AND APPARATUS FOR DETERMINING THE EFFECTIVENESS OF AN IMAGE TRANSFORMATION PROCESS

(75) Inventors: Scott David Wollenweber, Waukesha, WI (US); Alexander Ganin, Whitefish Bay, WI (US); Ravindra Manjeshwar, Glenville, NY (US); Girishankar Gopalakrishnan, Karnataka (IN); Evren Asma, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 1002 days.

(21) Appl. No.: 12/099,261

(22) Filed: Apr. 8, 2008

(65) Prior Publication Data

US 2009/0253980 A1 Oct. 8, 2009

(51) Int. Cl.
*A61B 6/03* (2006.01)
(52) U.S. Cl. .................................. 382/131; 600/428
(58) Field of Classification Search .............. 382/128, 382/131
See application file for complete search history.

(56) References Cited

U.S. PATENT DOCUMENTS

| | | | |
|---|---|---|---|
| 4,577,152 A | 3/1986 | Macovski | |
| 5,128,864 A | 7/1992 | Waggener | |
| 5,307,264 A | 4/1994 | Waggener | |
| 5,430,783 A | 7/1995 | Hu et al. | |
| 5,647,018 A | 7/1997 | Benjamin | |
| 5,673,300 A | 9/1997 | Chang | |
| 5,694,530 A | 12/1997 | Goto | |
| 5,720,291 A | 2/1998 | Schwartz | |
| 5,740,222 A | 4/1998 | Fujita et al. | |
| 5,900,878 A | 5/1999 | Goto et al. | |
| 5,920,660 A | 7/1999 | Goto | |
| 6,990,231 B2 | 1/2006 | Goto | |
| 7,039,451 B1 * | 5/2006 | Jhooti et al. | 600/413 |
| 7,116,808 B2 | 10/2006 | Ditt et al. | |
| 7,536,219 B2 * | 5/2009 | Mitschke | 600/425 |
| 2005/0113673 A1 * | 5/2005 | Avinash et al. | 600/413 |

(Continued)

FOREIGN PATENT DOCUMENTS

JP 08267292 A 10/1996
(Continued)

OTHER PUBLICATIONS

Manjeshwar et al, "Motion Compensated Image Reconstruction of Respiratory Gated PET/CT", 3rd IEEE International Symposium on Biomedical Imaging: Nano to Macro, 2006.*

(Continued)

*Primary Examiner* — Clayton E LaBalle
*Assistant Examiner* — Leon W Rhodes, Jr.
(74) *Attorney, Agent, or Firm* — The Small Patent Law Group; Dean D. Small (57) ABSTRACT

A method for determining the effectiveness of an image transformation process includes acquiring a four-dimensional (4D) image data set, sorting the 4D image data set into separate field-of-view bins using a temporal gating system generating a plurality of deformation vectors using the sorted 4D image data set, and using the plurality of deformation vectors to generate a transformation effectiveness value that is representative of the effectiveness of the image transformation process. The method further includes acquiring a respiratory signal, calculating a power spectrum of the respiratory signal, calculating a power spectrum for each of the plurality of deformation vectors, and comparing the power spectrum of the respiratory signal to the power spectrum of the plurality of deformation vectors to generate the transformation effectiveness value.

26 Claims, 9 Drawing Sheets

U.S. PATENT DOCUMENTS

2006/0178575 A1     8/2006    Piacsek et al.
2007/0205368 A1     9/2007    Heukensfeldt Jansen et al.

FOREIGN PATENT DOCUMENTS

JP             09156689 A      6/1997

OTHER PUBLICATIONS

Jean Thirion Et Al; Deformation Analysis to Detect and Quantify Active Lesions in Three-Dimensional Medical Image Sequences; IEEE Trans on Med Imaging vol. 18, No. 5, May 1999.

Nicholas Ayache (Ed.); Visualization of Multimodal Images for Neurosurgical Planning and Guidance, Lecture Notes in Computer Science, "Computer Vision, Virtual Reality and Robotics in Medicine", First International Conference, CVRMed '95, Nice, France, Apr. 1995 Proceedings; 10 pages.

Frederik Maes et al; Lecture Notes in Computer Science, "Computer-Aided Interactive Object Delineation Using an Intelligent Paintbrush Technique"; First International Conference, CVRMed '95, Nice, France, Apr. 1995 Proceedings pp. 77-83.

Jed Lengyel et al.; Lecture Notes in Computer Science, "Three-Dimensional Reconstructions and Volume Rendering of Intravascular Ultrasound slices Imaged on a Curved Arterial Path"; First International Conference, CVRMed '95, Nice, France, Apr. 1995 Proceedings pp. 399-405.

Robert A. Drebin et al.; "Volume Rendering"; Computer Graphics, vol. 22, No. 4, Aug. 1988; pp. 65-74.

Karel J Zuiderveld et al.; "Multi-Modal Volume Visualization Using Object-Oriented Methods"; 0-8186-7067-3/95, 1995 IEEE pp. 59-66 and 129.

Max A Viergever; "Integrated Presentation of Multimodal Brain Images", Brain Topography, vol. 5, No. 2, 1992; pp. 135-145.

Markus Hardwiger et al.; "High-Quality Two-Level Volume Rendering of Segmented Data Sets on Consumer Graphics Hardware"; 8 pgs.

Jean-Jose Jacq et al; "A Direct Multi-Volume Rendering Method. Application to Visual Assessment of 3-D Image Registration Algorithms"; 10 pgs.

Paul J Keller, PhD, et al.; "MR Angiography with Two-dimensional Acquisition and Three-Dimensional Display"; Radiology, Nov. 1989, pp. 527-532.

Philippe G. Lacroute; "Fast Volume Rendering Using a Shear-Warp Factorization of the Viewing Transformation"; Technical Report: CSL-TR-95-678; Stanford Center for Integrated Systems, ARPA/ONR Contracts N00039-91-C-0138, 175-6212-1, NSF Contract CCR-9157767; 236 pages.

Pascal Volino et al.; Efficient Self-collision Detection on Smoothly Discretized Surface Animations using Geometrical Shape Regularity; MIRALab Copyright © Information 1998; MIRALab, University of Geneva; 18 pages.

* cited by examiner

Resp = Red, Random = Blue, Good = Green

FIG. 9

Time (Sec) Resp

FIG. 10

Time (sec) Randam Signal

METHOD AND APPARATUS FOR DETERMINING THE EFFECTIVENESS OF AN IMAGE TRANSFORMATION PROCESS

BACKGROUND OF THE INVENTION

This invention relates generally to imaging systems capable of operation in multiple modalities, and more particularly to an apparatus and method for determining the effectiveness of an image transformation process.

Multi-modality imaging systems are capable of scanning using different modalities, such as, for example, Positron Emission Tomography (PET), Single Photon Emission Computed Tomography (SPECT), and Computed Tomography (CT). Conventional PET/CT imaging systems experience image quality that is highly affected by physiological patient motion. The quality of the acquired images may affect patient diagnosis.

Patient organ and lesion motion can be a significant source of image quality degradation. Respiratory motion is the most common involuntary motion encountered in PET/CT due to the required duration of PET scanning necessary to obtain clinically useful information. The respiratory motion may be particularly detrimental when a physician is determining the size of a lesion, determining the location of the lesion, or quantifying the lesion. By employing a cardiac and/or respiratory gating protocol during scan acquisition, images may be classified according to the physiological position in the cardiac/respiratory cycle. The gating technique can aid in correction for motion artifacts in images. Also, the image pathway of the nodule or other features of interest may be tracked.

Conventional methods for compensating for respiratory motion, such as by reducing the respiratory motion related artifacts, include using a device that measures an external respiratory signal to gate the PET data. During operation, the PET data is gated into separate bins over the respiratory cycle based on the respiratory signal. Given regular breathing cycles and sufficient imaging time-per-bin, the PET images will include the feature of interest.

However, while conventional methods are useful in reducing imaging artifacts, it is difficult in general for an operator to determine the effectiveness of the conventional image registration process. Specifically conventional imaging systems do not provide feedback to the operator to allow the operator to determine the effectiveness of a data or image transformation process and determine the accuracy of a transformation with regard to the size or location of the lesion of interest.

BRIEF DESCRIPTION OF THE INVENTION

In one embodiment, a method for determining the effectiveness of an image transformation process is provided. The method includes acquiring a four-dimensional (4D) image data set (x, y, z, time), sorting the 4D image data set into separate field-of-view bins using a temporal gating system generating a plurality of deformation vectors using the sorted 4D image data set, and using the plurality of deformation vectors to generate a transformation effectiveness value that is representative of the effectiveness of the image transformation process. The method further includes acquiring a respiratory signal, calculating a frequency power spectrum of the respiratory signal, calculating a frequency power spectrum for each of the plurality of deformation vectors, and comparing the power spectrum of the respiratory signal to the power spectrum of the plurality of deformation vectors to generate the transformation effectiveness value.

In another embodiment a multi-modality imaging system including a first modality unit, a second modality unit, and a computer operationally coupled to the first and second modality units is provided. The computer is programmed to acquire a four-dimensional (4D) image data set, sort the 4D image data set into separate field-of-view bins using a temporal gating system automatically generate a plurality of deformation vectors using the sorted 4D image data set, and use the plurality of deformation vectors to generate a transformation effectiveness value that is representative of the effectiveness of the image transformation process.

In a further aspect, a computer readable medium encoded with a program programmed to instruct a computer is provided. The computer readable medium is acquire a four-dimensional (4D) image data set, sort the 4D image data set into separate field-of-view bins using a temporal gating system, automatically generate a plurality of deformation vectors using the sorted 4D image data set, and use the plurality of deformation vectors to generate a transformation effectiveness value that is representative of the effectiveness of the image transformation process.

BRIEF DESCRIPTION OF THE DRAWINGS

FIG. is 3 a flowchart illustrating an exemplary method for determining the effectiveness of an image transformation process in accordance with an embodiment of the present invention.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 1:
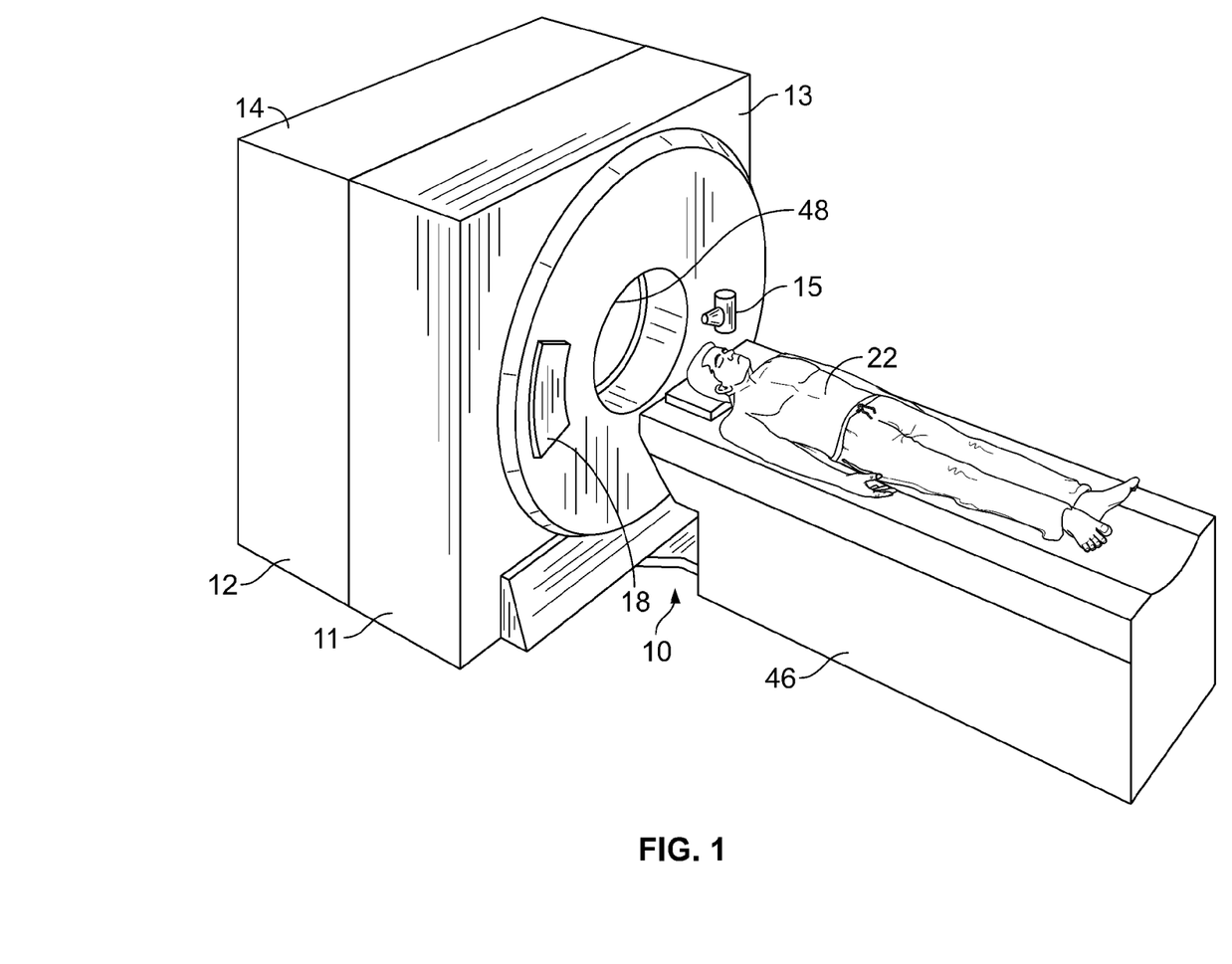
FIG. 1 is a pictorial view of an exemplary multi-modality imaging system in accordance with an embodiment of the present invention.

Various embodiments of the invention provide a diagnostic imaging apparatus 10 as shown in FIG. 1. Diagnostic imaging apparatus 10 may be any type of system for example, different types of medical imaging systems, such as an ultrasound imaging apparatus or a multi-modality imaging apparatus, among others, in which the phase of the transmitted signal is controlled and non-linearities with respect to the signal in an object of interest are significant. The various embodiments are not limited to medical imaging systems or imaging systems for imaging human subjects, but may include veterinary or non-medical systems for imaging non-human objects etc.

Figure 2:
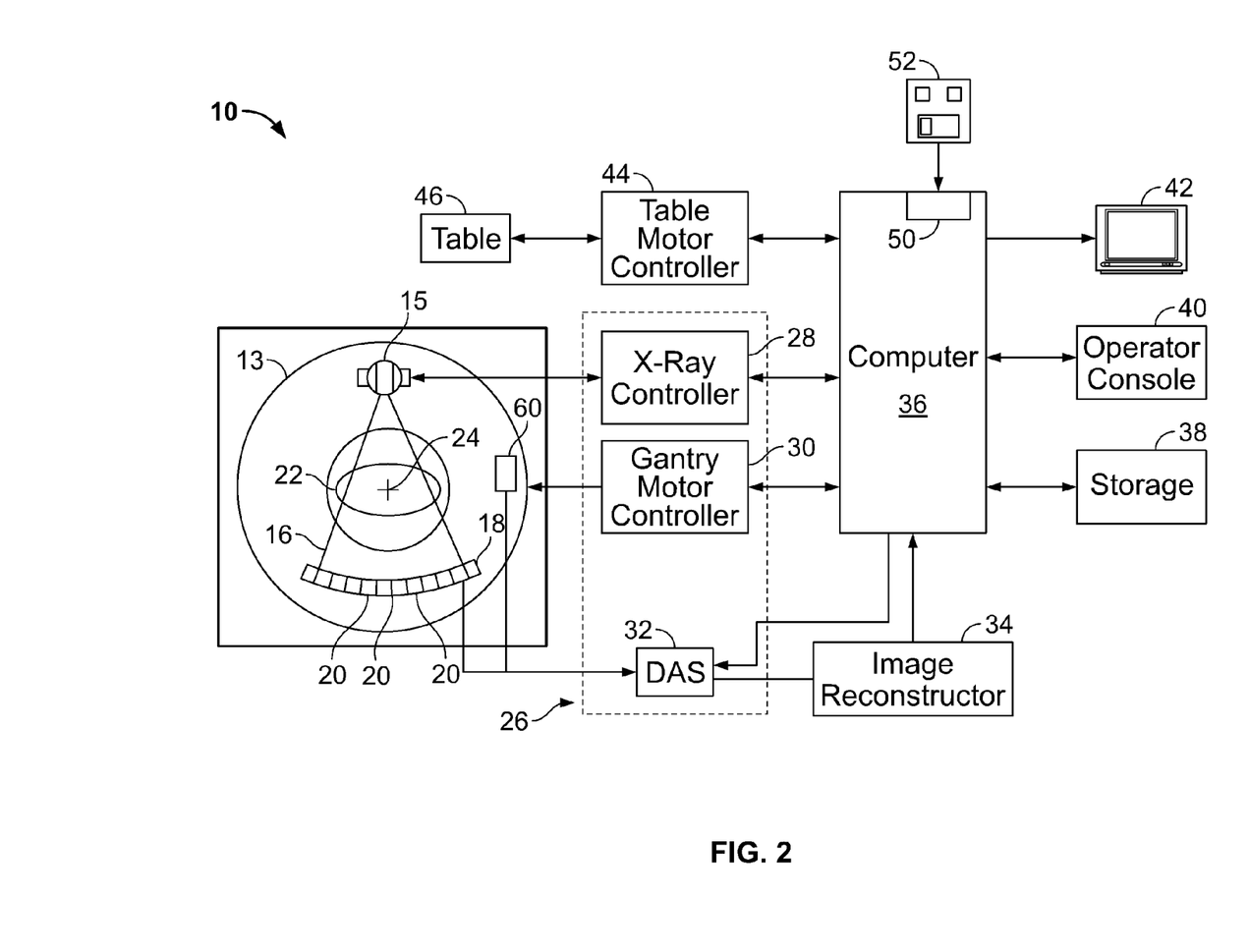
FIG. 2 is a block schematic diagram of the system illustrated in FIG. 1 in accordance with an embodiment of the present invention.

FIG. 1 is a pictorial view of an exemplary multi-modality imaging system 10 in accordance with an embodiment of the present invention. FIG. 2 is a block schematic diagram of the multi-modality imaging system 10 illustrated in FIG. 1 in accordance with an embodiment of the present invention. Referring to FIGS. 1 and 2, a multi-modality imaging system 10 is illustrated, and includes a first modality unit 11 and a second modality unit 12. The two modality units, 11 and 12, enable system 10 to scan an object or patient 22 in a first modality using the first modality unit 11 and to scan the object in a second modality using the second modality unit 12. System 10 allows for multiple scans in different modalities to facilitate an increased diagnostic capability over single modality systems. In one embodiment, multi-modality imaging system 10 is a Computed Tomography/Positron Emission Tomography (CT/PET) imaging system 10. Optionally modalities other than CT and PET are employed with system 10. The first modality unit 11, for example the CT imaging system includes a gantry 13, that has an x-ray source 15 that projects a beam of x-rays 16 toward a detector array 18 on the opposite side of gantry 13. Detector array 18 is formed by a plurality of detector rows that each include a plurality of detector elements 20, that together sense the projected x-rays that pass through an object, such as a medical patient 22. Each detector element 20 produces an electrical signal that represents the intensity of an impinging X-ray beam and hence allows estimation of the attenuation of the beam as it passes through object or patient 22. During a scan to acquire x-ray projection data, gantry 13 and the components mounted thereon rotate about a center of rotation 24. FIG. 2 shows only a single row of detector elements 20 (i.e., a detector row). However, a multislice detector array 18 includes a plurality of parallel detector rows of detector elements 20 such that projection data corresponding to a plurality of slices can be acquired simultaneously during a scan.

Rotation of gantry 13 and the operation of x-ray source 15 are governed by a control mechanism 26 of CT/PET system 10. Control mechanism 26 includes an x-ray controller 28 that provides power and timing signals to x-ray source 15 and a gantry motor controller 30 that controls the rotational speed and position of gantry 13. A data acquisition system (DAS) 32 in control mechanism 26 samples analog data from detector elements 20 and converts the data to digital signals for subsequent processing. An image reconstructor 34 receives the sampled and digitized x-ray data from DAS 32 and performs high-speed image reconstruction. The reconstructed image is applied as an input to a computer 36 that stores the image in a storage device 38. Computer 36 also receives commands and scanning parameters from an operator via console 40 that has a keyboard or other user inputs. An associated visual display unit 42 allows the operator to observe the reconstructed image and other data from computer.

The operator supplied commands and parameters are used by computer 36 to provide control signals and information to DAS 32, x-ray controller 28 and gantry motor controller 30. In addition, computer 36 operates a table motor controller 44 that controls a motorized table 46 to position patient 22 in gantry 13. Particularly table 46 moves at least a portion of patient 22 through a gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

CT/PET system 10 also includes the second imaging modality 12, for example the PET imaging modality. The PET imaging modality 12 includes a PET emission detector 60 including a plurality of detector elements (not shown). The PET emission detector 60 and CT detector array 18 both detect radiation and are both referred to herein as radiation detectors. In one embodiment, CT/PET system 10 is a Discovery Series CT/PET system commercially available from General Electric Medical Systems, Waukesha Wis., and configured as herein described. In another embodiment, CT/PET system 10 is a Hawkeye CT/PET/SPECT system also commercially available from GE Healthcare Waukesha Wis., and configured as herein described. Additionally although described in a medical setting, it is contemplated that the benefits of the invention described herein may also accrue to all multi-modality imaging systems and also non-medical imaging modalities, for example non-destructive testing, airport security, etc.

In the exemplary embodiment, the x-ray source 15 and the detector array 18 are rotated with a gantry 13 within the imaging plane and around the patient 22 to be imaged such that the angle at which the x-ray beam 16 intersects the patient 22 constantly changes. A group of x-ray attenuation measurements, i.e., projection data, from the detector array 18 at one gantry angle is referred to as a "view". A "scan" of the patient 22 comprises a set of views made at different gantry angles, or view angles, during one revolution of the x-ray source 15 and detector 18.

In an axial scan, the projection data is processed to construct an image that corresponds to a two-dimensional slice taken through the patient 22. One method for reconstructing an image from a set of projection data is referred to in the art as the filtered back projection technique. This process converts the integral attenuation measurements into an image representing attenuation of the patient in each pixel. The attenuation measurements are typically converted into units of CT numbers or Hounsfield units.

To reduce the total scan time, a "helical" scan may be performed. To perform a "helical" scan, the patient 22 is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically prior to the filtered back projection process, the data is weighted according to a helical weighing factor that is a function of both the gantry angle and detector angle. The weighted data is then processed to generate CT numbers and to construct an image that corresponds to a two dimensional slice taken through the patient 22. During operation of multi-slice CT/PET system 10, multiple projections are acquired simultaneously faith multiple detector rows. Similar to the case of helical scan, weighting functions are applied to the projection data prior to the filtered back projection process.

During operation of the PET imaging system 12, positrons, i.e. positively charged electrons or anti-electrons, are emitted by radionuclides that have been prepared using a cyclotron or other device. The radionuclides most often employed in diagnostic imaging are fluorine-18 (18F), carbon-11 (11C), nitrogen-13 (13N), and oxygen-15 (15O). Radionuclides are employed as radioactive tracers called "radiopharmaceuticals" by incorporating the radionuclides into substances such as glucose or carbon dioxide.

In typical use, the radiopharmaceutical is injected into a patient, such as patient 22, and accumulates in an organ, vessel or the like, that is to be imaged. It is known that specific radiopharmaceuticals become concentrated within certain organs or, in the case of a vessel, that specific radiopharmaceuticals will not be absorbed by a vessel wall. The process of concentrating often involves processes such as glucose metabolism fatty acid metabolism and protein synthesis.

After the radiopharmaceutical becomes concentrated within an organ of interest and while the radionuclides decay, the radionuclides emit positrons. The positrons travel a vera short distance before they encounter an electron and, when the positron encounters an electron, the positron is annihilated and converted into two photons. This annihilation event is characterized by two features that are pertinent to imaging and particularly to medical imaging using PET. First, each annihilation photon has an energy of approximately 511 keV upon annihilation. Second, the two annihilation photons are directed in substantially opposite directions.

In PET imaging, if the general locations of annihilations can be identified in three dimensions, a three dimensional image of an organ of interest can be reconstructed for observation, analysis, etc. To detect annihilation locations, a PET camera, for example, emission detector 60 is employed. The exemplary PET camera includes a plurality of detectors and a processor that, among other things, includes coincidence detection circuitry.

The coincidence circuitry (not shown) identifies essentially simultaneous pulse pairs that correspond to detectors that are essentially on opposite sides of the imaging area. Thus, a simultaneous pulse pair indicates that an annihilation event has occurred on a straight line between an associated pair of detectors. Over an acquisition period of a few minutes, millions of annihilations are recorded, and each annihilation is associated with a particular detector pair via, for example, DAS 32. After an acquisition period, recorded annihilation data can be used via any of several different well-known back projection procedures to construct the three-dimensional image of the organ of interest.

Figure 3:
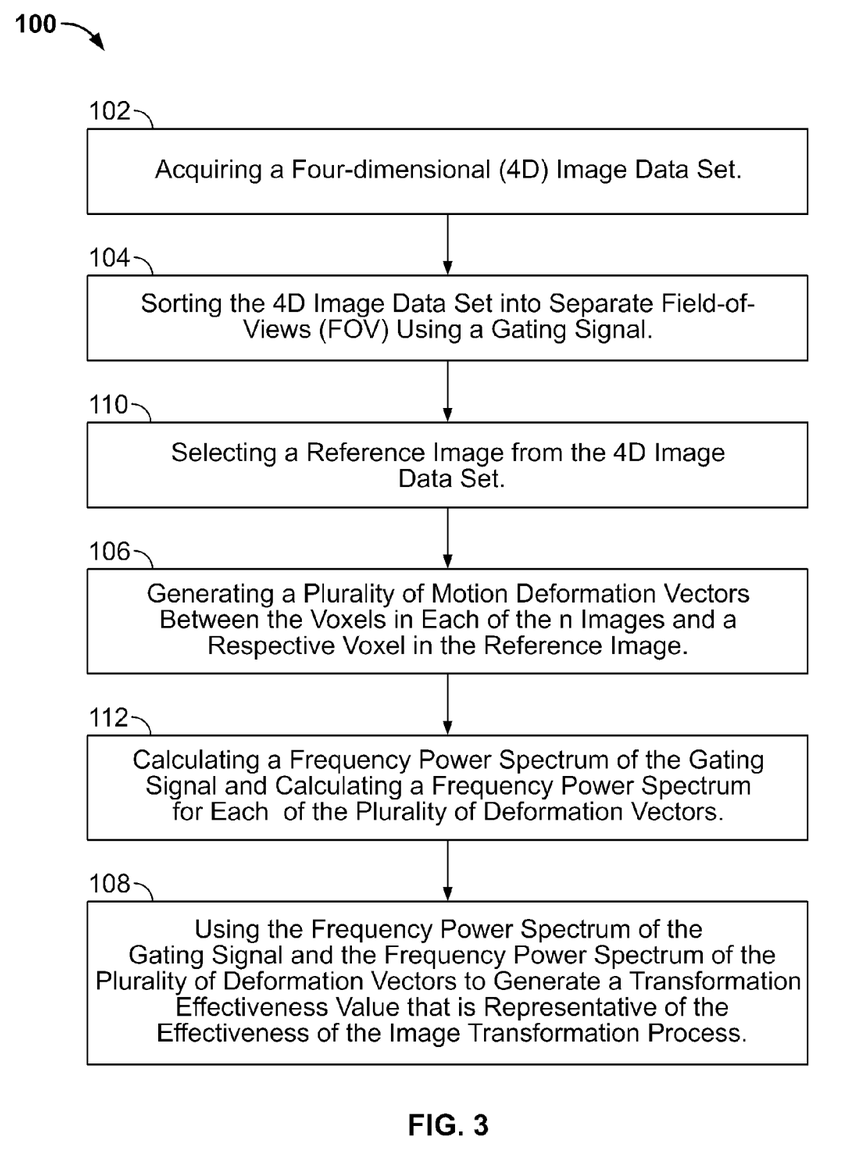

FIG. 3 is a flowchart illustrating an exemplary method 100 for determining the effectiveness of an image transformation process. The method 100 includes acquiring 102 a four-dimensional (4D) image data set. In the exemplary embodiment acquiring 102 may include scanning the patient 22 to generate the 4D image data set, downloading the 4D image data set from the memory installed in imaging system 10, or downloading the 4D image data set from an external source. Method 100 also includes sorting 104 the 4D image data set into separate field-of-views (FOV) or temporal bins using a temporal motion signal, such as the signal acquired using a motion detector 70 (shown in FIG. 2). The method 100 also includes generating 106 a plurality of deformation vectors using the sorted 4D image data set, and using 108 the plurality of deformation vectors to generate a transformation effectiveness value that is representative of the effectiveness of the image transformation process.

Acquiring 102 includes scanning an object, such as a test phantom or the patient 22, using the PET imaging system 12. In the exemplary embodiment acquiring 102 includes performing a whole-body scan of the patient 22 to generate a 4D image data set. As discussed above, in PET imaging, if the general locations of annihilations can be identified in three dimensions, a three-dimensional image of an organ of interest can be reconstructed for observation. All the data gathered from multiple scans of the patient is to be considered one data set. Each data set can be broken up into smaller units, either pixels or voxels. When the data set is a three-dimensional data set, the image is displayed in units called voxels. A voxel is a volume element in three-dimensional space that can be referenced using three-dimensional coordinates, usually x, y and z. Each voxel is typically surrounded by twenty-six other voxels. These twenty-six voxels can be considered the twenty-six connected neighbors of the original voxel. The data includes a plurality of line-integrals of the to-be-determined tracer concentration relating to the position and/or orientation of the line of response (LOR) on which the annihilation events occurred and the integral of the events over the measurement time. Typically events with the same or almost the same LOR are added to from a so-called line integral. Furthermore, line integrals, that belong to parallel LORs, are grouped together. Such a group is called a projection. The data structure containing projections from 0 to 180 degrees is usually referred to as sinogram.

The PET image data may be stored in the form of a list. 'List mode' data represents a capture by the PET detector 60 of coincidence event pairs in the form of an ordered event list for example, a chronologically ordered event list. List file events may be played back into a new scan prescription to produce derivations of the original scan. For example, the new scan prescription may specify a different frame duration or (gated) bin size. Therefore, smaller temporal sets of data may be evaluated, gaining higher temporal resolution.

Figure 5:
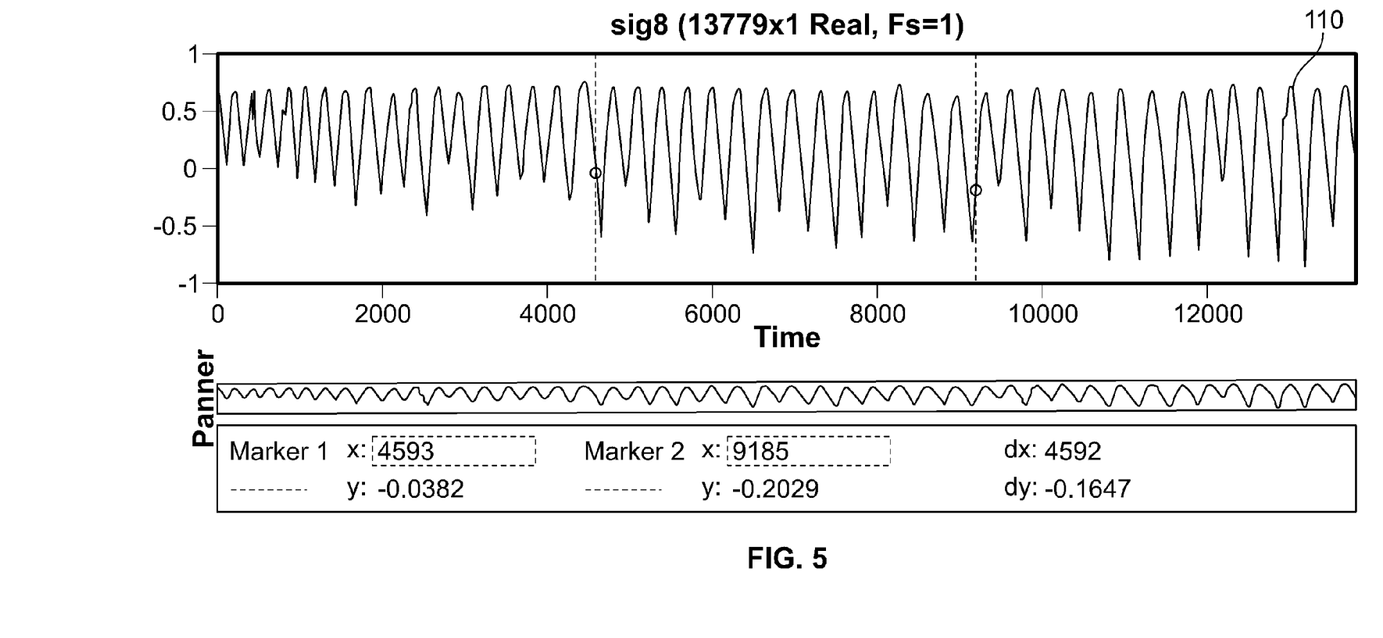
FIG. 5 is a graphical illustration of an exemplary respiratory motion signal acquired in accordance with an embodiment of the present invention.
Figure 6A:
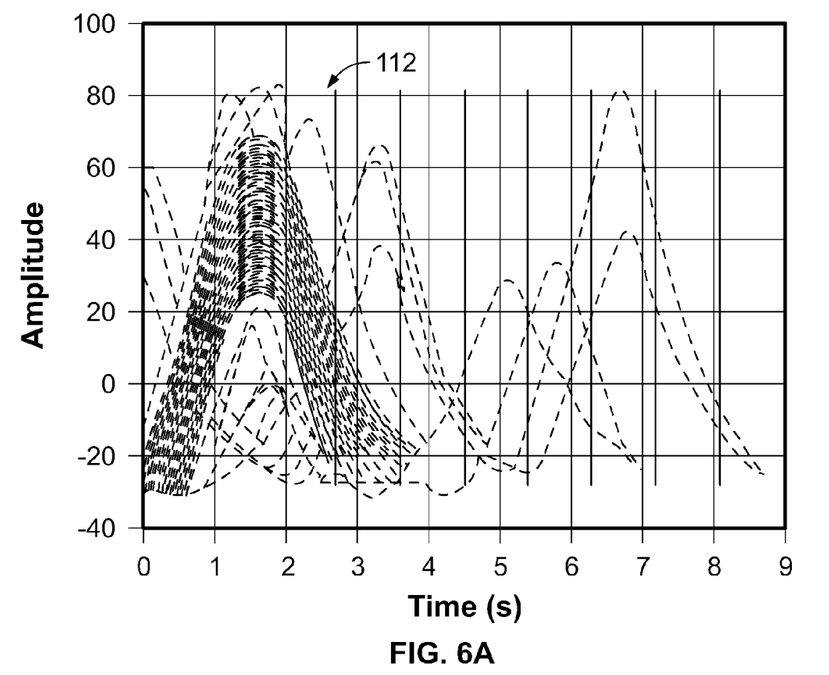
FIG. 6 is a graphical illustration of exemplary power spectrums generated using the respiratory signals shown in FIG. 5 in accordance with an embodiment of the present invention.

Method 100 also includes sorting 104 the 4D image data set. This includes the three-dimensional image data gated using a temporal motion signal acquired using the motion detector 70, for example. Specifically method 100 includes acquiring a motion or respiratory signal using a temporal gating system. The respirator signal may be acquired, for example, by using respiratory sensor 70 (shown in FIG. 2). The respiratory or motion sensor 70 generates a signal, for example respiratory signal or trace 110 (shown in FIG. 5), which is representative of the respiratory motion of the patient 22. Optionally imaging system 10 may use a device that injects a trigger signal into the PET and/or CT data stream. Specifically the respiratory trace 110, shown in FIG. 5, is gated to generate a plurality of respiratory traces or signals 112, shown in FIG. 6A, that are gated allowing subsequent sorting of the data into equal-duration bins within the trigger-to-trigger intervals as shown in FIG. 6A.

The combination of the 3D image data and the data produced using the acquired respiratory signal or traces are referred to herein as a 4D image data set. For example, the respiratory cycle generated using respiratory sensor 70 is divided into time intervals or phases based on the detected changes in the respiratory cycle.

Figure 4:
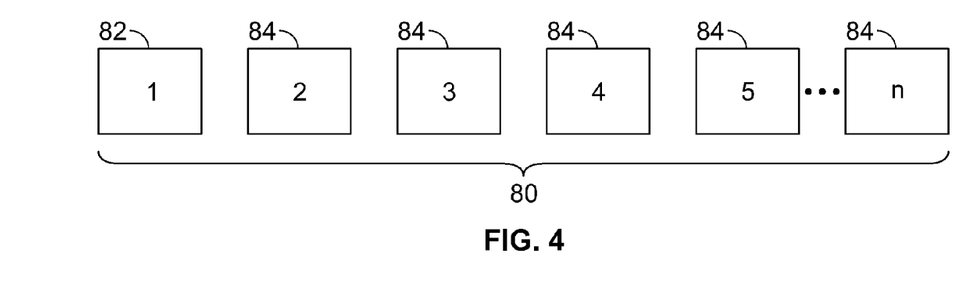
FIG. 4 is block schematic diagram illustrating a plurality of gates or bins to receive imaging data in accordance with an embodiment of the present invention.

Method 100 further includes sorting 104 the 4D image data set into separate field-of-views or bins 80 as shown in FIG. 4. The portions of the stream of sinogram data associated with the time intervals are gated into associated bins (shown as bins 80(1)-80(n) in FIG. 4, or phases of the respiratory cycle. Each bin 80 belongs to a certain motion state. In other words, when an organ having a more or less periodical motion is imaged, the image data is rearranged such that projections acquired at a similar phase or motion state are binned into the same temporal bin. The decision as to which bin 80 an event belongs may be made on the basis of information acquired using the motion sensor, that may in the exemplary embodiment be the respiratory sensor 70. A three dimensional image or frame may be reconstructed from each bin 80.

Method 100 also includes applying a motion correction to the 4D image data set. In the exemplary embodiment, the motion correction may be derived from each of the PET data, the CT data or both, and compared to the respiratory tracker signal generated using the motion sensor 70. Optionally the motion may be based locally to a feature-of-interest, for example, a test object may be placed on the patient 22 and monitored for movement, instead of monitoring the patient's breathing, etc. The motion may also be extracted from a patient or organ surface, including in the vicinity of the respiratory sensor 70.

Figure 6B:
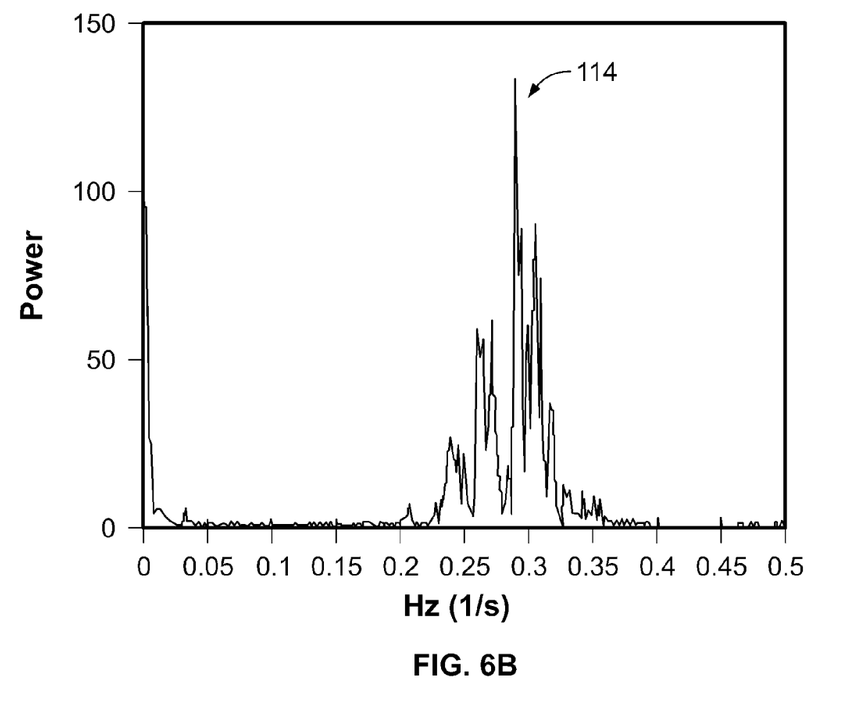
Figure 7:
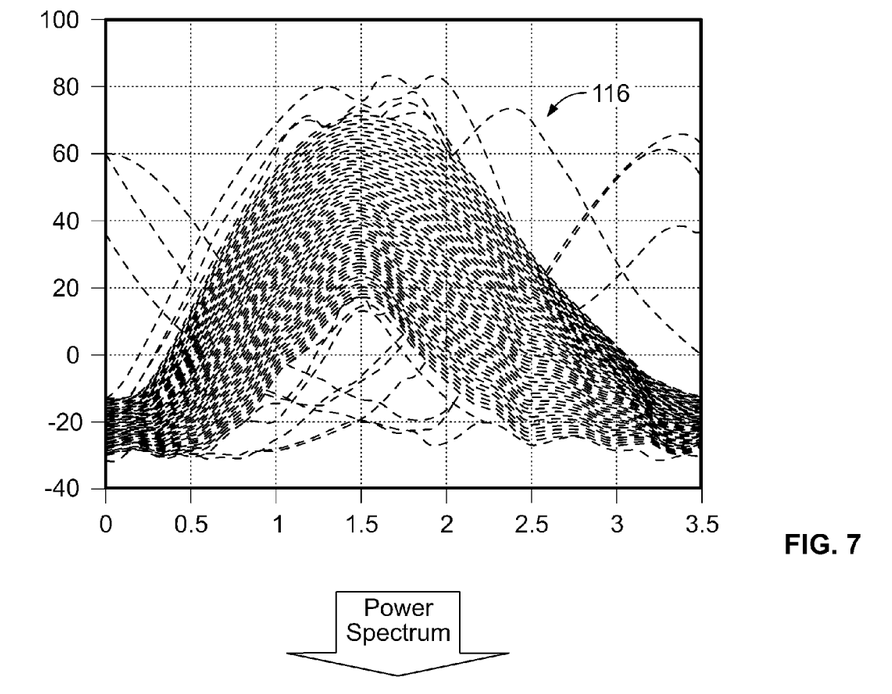
FIG. 7 is a graphical illustration of an exemplar average respirator signal acquired for each bin in accordance with an embodiment of the present invention.
Figure 8:
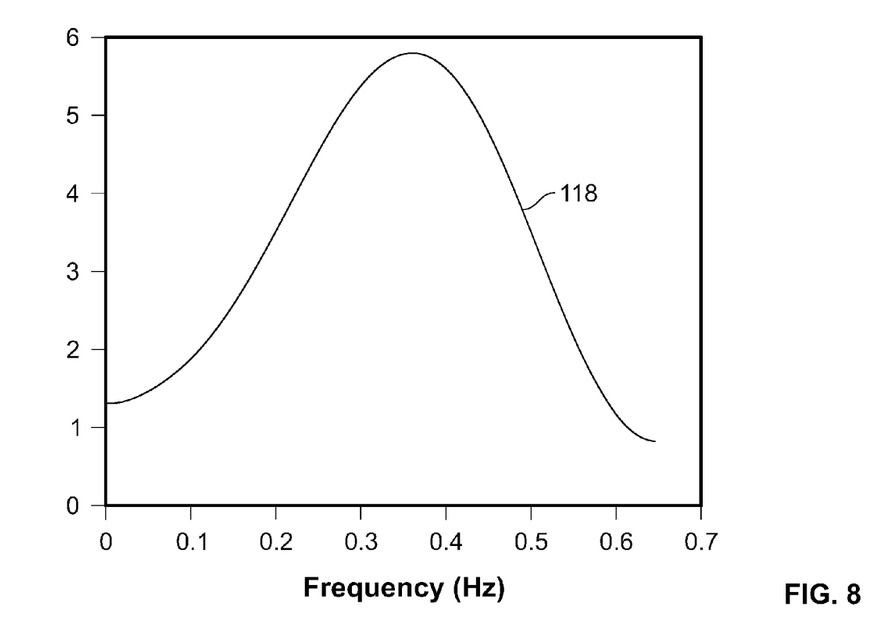
FIG. 8 is a graphical illustration of the power spectrum of the average respiratory signals shown in FIG. 7 in accordance with an embodiment of the present invention.
Figure 9:
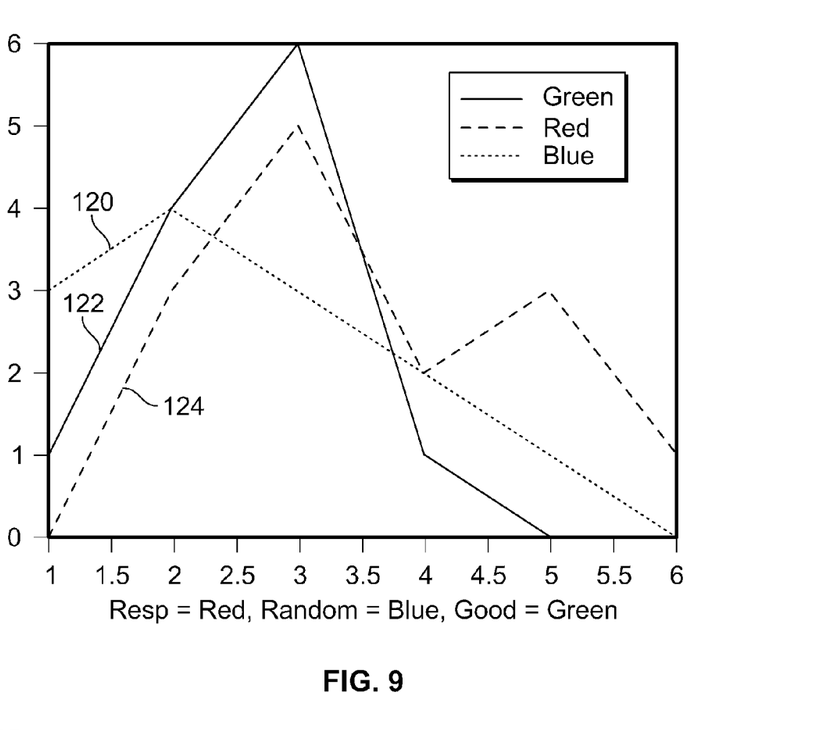
FIG. 9 is a graphical illustration of an average respiratory trace plotted in magnitude versus time in accordance with an embodiment of the present invention.
Figure 10:
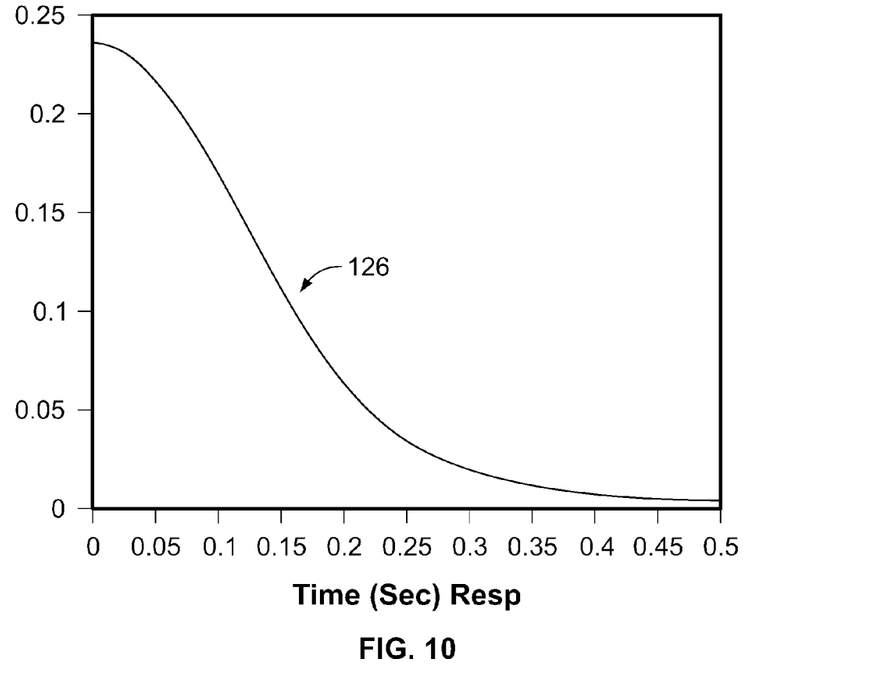
FIG. 10 is a graphical illustration of the power spectrum of the respiratory trace shown in FIG. 9 after motion correction has been applied in accordance with an embodiment of the present invention.
Figure 11:
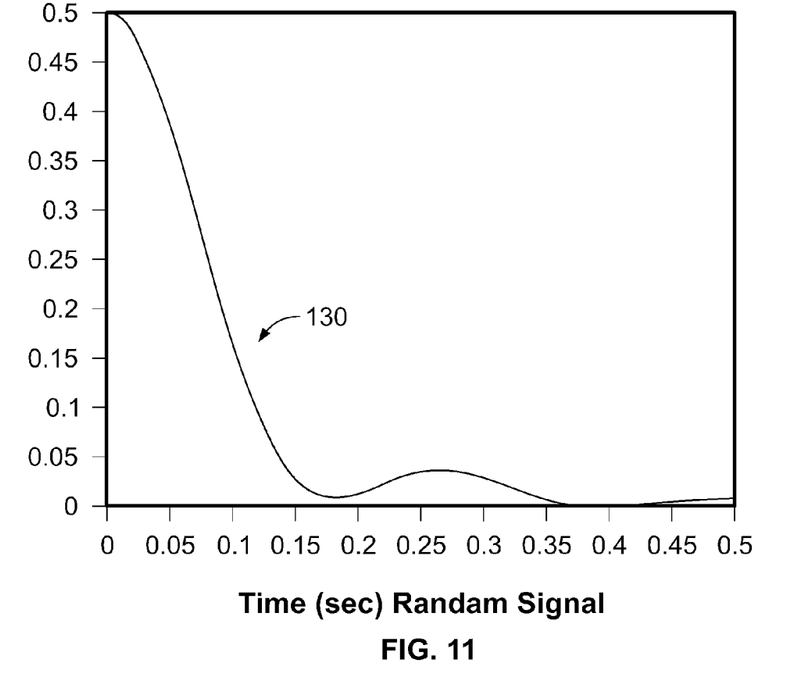
FIG. 11 is a graphical illustration of the power spectrum of an exemplary respiratory signal or trace in accordance with an embodiment of the present invention.
Figure 12:
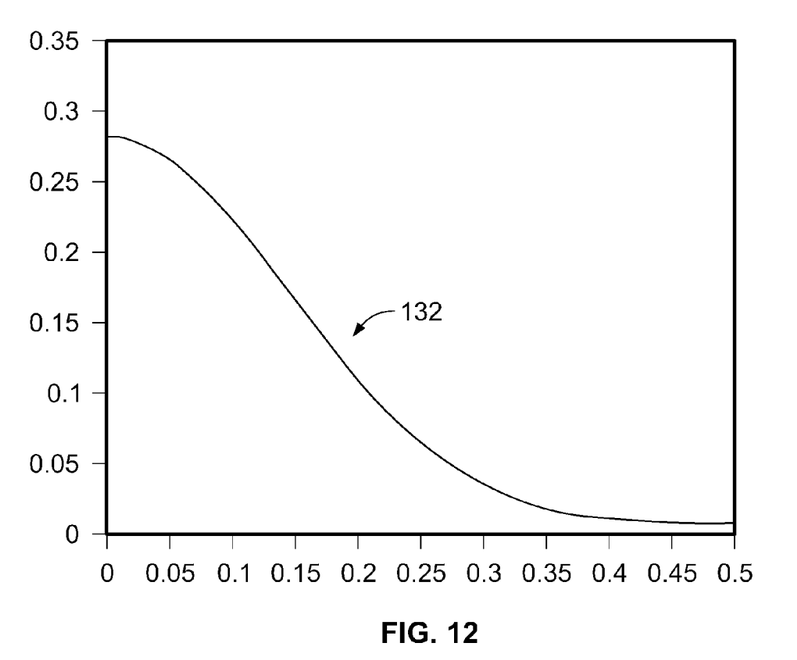
FIG. 12 is a graphical illustration of an exemplary respiratory signal or trace of a "good" motion vector in accordance with an embodiment of the present invention.

For example, as discussed above, FIG. 6A is a graphical illustration of a plurality of respiratory signals 112 acquired using the motion detector 70 wherein the respiratory signal trace has been restarted at t=0 using each trigger event. FIG. 6B is a graphical illustration of a frequency power spectrum 114 of the respiratory signals shown in FIG. 6A. Optionally the power spectrum 114 may be calculated following removal of some non-typical cycles from the data 112. FIG. 7 is another example plot of a plurality of respiratory signals 116. FIG. 8 is a graphical illustration of a power spectrum 118 of the respiratory signals 116 shown in FIG. 7. Power spectrum as used herein, represents a portion of a signal's power, i.e. energy per unit time, falling within given frequency bins. The power spectra 114 and/or 118 may be generated using, for example, a discrete Fourier transform. FIG. 9 is a graphical illustration of an average respiratory trace 124 plotted in magnitude versus time. In the exemplary embodiment, applying a motion correction to data with this average respiratory trace 124 includes applying a motion correction vector with average trace 122 to some of the data but a random motion correction vector 120 to other portions of the data. FIG. 10 is a graphical illustration of a power spectrum 126 constructed from data shown as the average respiratory trace 124 shown in FIG. 9. FIG. 11 is a graphical illustration of a power spectrum 130 of an exemplary random motion vectors, and FIG. 12 is a graphical illustration of an exemplary respiratory signal or trace of a set of motion vectors 132 which mimic the power spectrum of the respiratory trace 124. That is, on a subset of the data the transformation process is performed successfully as will be discussed below.

Method 100 also includes generating a plurality of deformation vectors using the sorted 4D image data set. As discussed above, each 3D image or data image set stored in each respective bin 80 includes a plurality of voxels that are points in three-dimensional space that can be referenced using three-dimensional coordinates, usually x, y and z. A deformation vector represents a motion and/or deformation of the object or voxel(s) of interest, such as the motion of patient 22, at a certain point of time. Specifically for each image voxel and for each gate or bin 80, the vector magnitude [v] (or set of magnitudes) and components [x,y,z], referred to herein as the deformation components, are stored in the memory. Since all voxels need not represent a motion similar to the respiratory signal tracker, representative landmarks from the data can be used as well.

In the exemplary embodiment, method 100 includes selecting 110 a reference image from the 4D image data set, for example, selecting one of the bins 80, such as bin 82 shown in FIG. 4), as the reference image. The remaining bins 84 are then mapped to the reference bin or image 82 to generate the motion deformation vectors. In one embodiment, each voxel in each of bins 84 is mapped to a respective reference voxel in the reference image or bin 82. Optionally the total magnitude of the voxel motion in each gate or bin 80 may be used to generate the deformation vectors. The per-voxel power spectrum, over the gates or bins 80 is then calculated using either the deformation components discussed above, or the total magnitude of the voxel motion calculated for each respective gate.

Method 100 also includes comparing the calculated per-voxel power spectrum for each voxel in the bins 80 to the separately measured respiratory signal power spectrum shown in FIG. 10. For example, the motion vector of each deformation is calculated for each image voxel and for each gate or bin 80. The resultant calculations are then stored. For example, the vector magnitude and direction components for each motion deformation vector are stored. In one embodiment, comparing the power spectrums includes summing the power spectrum products. Specifically once, the power spectrum has been determined for each of the respective deformation vectors, method 100 further includes multiplying the power spectrums for each voxel in each respective bin 80 together to generate a power spectrum product. In the exemplary embodiment, the power spectrum product is the image transformation effectiveness value.

In the exemplary embodiment, to determine whether the transformation process is performed successfully an image transformation effectiveness value, for example a numerical value, is generated and to enable an operator to quickly assess the effectiveness of the transformation process. In the exemplary embodiment, the image transformation effectiveness value is defined between a range of 0 and 1. For example, if the image transformation effectiveness value calculated is approximately 1, then the applied deformation across the gates or bins 80 has a temporal frequency signature that agrees with the separately-measured respiratory signal and the quality of the deformation process is more likely to be high. However, as the image transformation effectiveness value approaches 0, e.g. the applied deformation across the gates or bins 80 does not have a temporal frequency signature that agrees with the separately-measured respiratory signal deformation, the quality of the deformation process is less than fully effective. In another embodiment, the deformation vectors may be "de-weighted" when the temporal frequency signature does not follow that of the independently-derived respiratory signal.

A technical effect of method 100 is to provide a fully automatic method of assessing the correspondence between a frame-to-frame deformation and an independently measured waveform correlated to the patient motion. Specifically, following the calculation of either local or global voxel-based deformation vectors, if the applied deformation across gates or bins has a temporal frequency that agrees with the independently measured respiratory signal, then the quality of the deformation is more likely to be high, e.g. the registration between images or the registration between sub-components within two images is good. If a deformation, however, does not have the same temporal frequency then it likely represents more random movement of data and thus is not representative of the type of motion expected from the respiration waveform. In operation, method 100 produces net quality assurance measure, i.e. the sum or the transformation effectiveness value, and de-emphasizes deformations that do not agree with the independently derived motion signal. Method 100 may be applied to either a global deformation registration or one based on local information. Further, method 100 may be implemented no matter what information went into the registration, such as CT-CT, PET-PET or some combination thereof.

Figure 13:
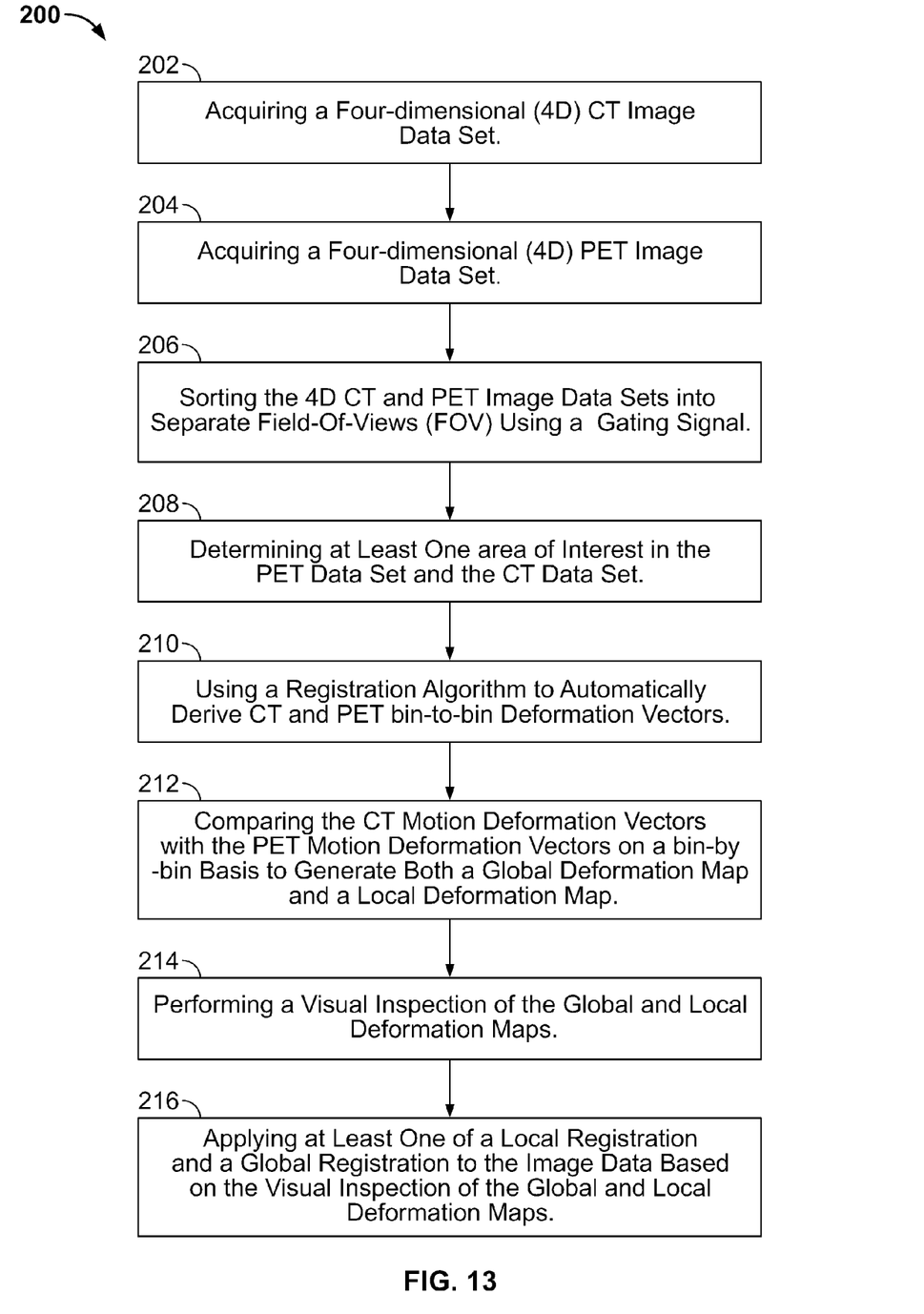
FIG. 13 is a flowchart illustrating another exemplary method for determining the effectiveness of an image transformation process in accordance with an embodiment of the present invention.

FIG. 13 is another exemplary method 200 for determining the effectiveness of an image transformation process. In the exemplary embodiment, method 200 utilizes computer generated deformation vectors that are derived using 4D CT image data and 4D PET data. Specifically, method 200 utilizes a comparison of frame-to-frame deformation vectors as derived from the CT image data to those derived from the PET image data. Examples of similarity metrics between two vectors are the bending and stretching errors. If the deformation vectors fulfill a similarity criterion, e.g. the bending or stretching errors do not exceed a predetermined threshold, the CT and PET deformation vectors are combined to generate a final optimized deformation vector. The CT and PET deformation vectors are also combined to generate a numerical feedback, for example, to generate the image transformation effectiveness value that is representative of the quality of the PET to CT motion similarity. This similarity metrics, e.g. the bending and stretching errors, may also be constrained locally to a feature in the PET data, for example constrained to a lesion or other feature of interest in the CT and PET images.

In the exemplary embodiment, method 200 includes acquiring a four-dimensional (4D) CT image data set and acquiring a four-dimensional 4D PET image data. As discussed above, acquiring the CT and PET image data set may include scanning the patient 22 to generate the 4D CT and PET image data sets, downloading the CT and PET image data sets from the memory installed in imaging system 10, or downloading the CT and PET image data sets from an external source. Method 200 also includes sorting 206 the 4D CT image data sets and the 4D PET image data sets into separate field-of-views (FOV) or temporal bins using a temporal motion signal, such as the signal acquired using a motion detector 70 (shown in FIG. 2). In the exemplary embodiment, the PET images utilize the CT binned images for CT-based attenuation correction, and the bins are assumed to describe the same state of motion between the PET and CT data. Moreover, binning may refer to several types of sorting applied to the data, and is the same for both datasets.

Method 200 further includes determining 208 at least one area-of-interest in the PET data set and/or the CT data set. The determination may be performed either manually via a user inspection, or may be performed automatically using a computer algorithm. Method 200 further includes using 210 a registration algorithm to automatically derive CT and PET bin-to-bin deformation vectors that describe the motion between bins. In the exemplary embodiment, the deformation vectors are derived or calculated as described above with respect to method 100. In the exemplary embodiment, the CT imaging system uses a first registration algorithm to derive the motion deformation vectors and the PET imaging system uses a second different algorithm to derive or calculate the motion deformation vectors. Optionally the CT and PET imaging system use the same registration algorithm to calculate each of the CT and PET motion deformation vectors however the reference gate is the same for PET and CT.

Method 200 further includes comparing 212 the CT motion deformation vectors with the PET motion deformation vectors. Comparing 212 includes examining or noting the similarities or differences of the CT and PET motion deformation vectors, on a bin-by-bin basis, to generate both a global deformation map representative of the motion, such as root mean squared error (RMSE), as to generate as a local deformation map that is representative of the motion in the vicinity of the feature or reference image set, for example a lesion of interest. An exemplary metric is then generated per feature to describe the motion similarity in the vicinity of the feature of interest. The method 200 further includes performing 214 a visual inspection of the global and local maps to ensure the similarity for user inspection and acceptance. In the exemplary embodiment, the visual inspection is performed by an operator using reconstructed CT and PET images. Based on the user inspection, method 200 further includes applying 216 a local registration, for example a registration per feature of interest, applying a global registration, and/or combining the global and local registrations to generate the transformation effectiveness value. Optionally a combination of the CT, PET, local and global registrations may be used to generate the transformation effectiveness value.

The methods and apparatus described herein provide a fully automatic method of generating an image registration or transformation effectiveness value that facilitates allowing an operator to determine the effectiveness of the registration process. A technical effect of the above describes methods is to increase the accuracy of identifying and location lesions and other features desired to be observed by the operator.

Some embodiments of the present invention provide a machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firm-ware" are interchangeable, and include any computer program stored in memory for execution by a computer, including RAM memory ROM memory EPROM memory EEPROM memory and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for determining the effectiveness of an image transformation process comprising:
   acquiring a four-dimensional (4D) image data set;
   sorting the 4D image data set into separate field-of-view bins using a gating system;
   generating a plurality of deformation vectors using the sorted 4D image data set; and
   generating a transformation effectiveness value directly from the plurality of deformation vectors, the transformation effectiveness value being representative of the effectiveness of the image transformation process.

2. A method in accordance with claim 1 wherein acquiring a four-dimensional (4D) image data set further comprises performing a whole-body PET scan to generate the 4D image data set.

3. A method in accordance with claim 1 further comprising applying a motion correction to the 4D image data set.

4. A method in accordance with claim 1, wherein the 4D image data set includes a reference image and n images each having a plurality of voxels, said method further comprising:
   selecting the reference image from the 4D image data set; and
   generating a motion deformation vector between the voxels in each of the n images and a respective voxel in the reference image to generate the plurality of motion deformation vectors.

5. A method for determining the effectiveness of an image transformation process comprising:
   acquiring a four-dimensional (4D) image data set;
   sorting the 4D image data set into separate field-of-view bins using a gating system;
   generating a plurality of deformation vectors using the sorted 4D image data set; and comparing a power spectrum of a respiratory signal to a power spectrum of the plurality of deformation vectors to generate the transformation effectiveness value.

6. A method in accordance with claim 1 further comprising:
acquiring a respiratory signal;
calculating a frequency power spectrum of the respiratory signal; and
calculating an average frequency power spectrum for the plurality of deformation vectors; and
comparing the power spectrum of the respiratory signal to the average power spectrum of the plurality of deformation vectors to generate the transformation effectiveness value.

7. A method in accordance with claim 1 further comprising:
acquiring a motion signal using the temporal gating system;
calculating a frequency power spectrum for the motion signal to generate a motion signal power spectrum;
calculating a frequency power spectrum for each of the plurality of deformation vectors to generate a plurality of deformation vector power spectrums; and
using the motion signal power spectrum and the deformation vector power spectrums to generate the transformation effectiveness value.

8. A method in accordance with claim 1 further comprising:
acquiring a respiratory signal;
calculating a frequency power spectrum of the respiratory signal to generate a respiratory signal power spectrum;
calculating a frequency power spectrum for each of the plurality of deformation vectors to generate a plurality of deformation vector power spectrums; and
summing the products of the respiratory signal power spectrum and the deformation vector power spectrums to generate the transformation effectiveness value.

9. A method in accordance with claim 1 further comprising scanning a patient using a Positron Emission Tomography (PET) imaging system.

10. A method for determining the effectiveness of an image transformation process comprising:
acquiring a four-dimensional (4D) CT image data set;
acquiring a four-dimensional (4D) PET image data set;
sorting the CT and PET image data sets into separate field-of-view bins using a temporal gating system;
generating a plurality of deformation vectors using the sorted CT and PET image data sets; and
generating a transformation effectiveness value directly from the plurality of deformation vectors, the transformation effectiveness value being representative of the effectiveness of the image transformation process.

11. A method in accordance with claim 10 further comprising using a registration algorithm to automatically derive a CT and PET bin-to-bin deformation vectors.

12. A method in accordance with claim 10 further comprising:
automatically deriving CT and PET bin-to-bin deformation vectors;
comparing the CT and PET deformation vectors on a bin-by-bin basis; and
generating at least one of a global measure and a local measure of the comparison.

13. A method in accordance with claim 10 further comprising:
automatically deriving CT and PET bin-to-bin deformation vectors;
comparing the CT and PET deformation vectors on a bin-by-bin basis; and
generating a root mean squared error based on the comparison.

14. A method in accordance with claim 10 further comprising:
automatically deriving CT and PET bin-to-bin deformation vectors;
comparing the CT and PET deformation vectors on a bin-by-bin basis; and
generating at least one of a global registration map and a local registration map based on the comparison.

15. A method in accordance with claim 10 further comprising
automatically deriving CT and PET bin-to-bin deformation vectors;
comparing the CT and PET deformation vectors on a bin-by-bin basis;
generating at least one of a global motion registration map and a local motion registration map based on the comparison; and
generating at least one of a local registration, a global registration, and a combined local and global registration using at least one of the global motion registration map and a local motion registration map to generate the transformation effectiveness value.

16. A multi-modality imaging system comprising a first modality unit, a second modality unit, and a computer operationally coupled to the first and second modality units, wherein the computer is programmed to:
acquire a four-dimensional (4D) image data set;
sort the 4D image data set into separate field-of-view bins using a temporal gating system;
automatically generate a plurality of deformation vectors using the sorted 4D image data set; and
generate a transformation effectiveness value directly from the plurality of deformation vectors, the transformation effectiveness value being representative of the effectiveness of the image transformation process.

17. A multi-modality imaging system in accordance with claim 16, wherein the 4D image data set includes a reference image and n images each having a plurality of voxels, said computer is further programmed to:
select the reference image from the 4D image data set; and
generate a motion deformation vector between the voxels in each of the n images and a respective voxel in the reference image to generate the plurality of motion deformation vectors.

18. A multi-modality imaging system in accordance with claim 16, wherein said computer is further programmed to:
acquire a respiratory signal;
calculate a frequency power spectrum of the respiratory signal;
calculate a frequency power spectrum for each of the plurality of deformation vectors; and
compare the power spectrum of the respiratory signal to the power spectrum of the plurality of deformation vectors to generate the transformation effectiveness value.

19. A multi-modality imaging system in accordance with claim 16, wherein said computer is further programmed to:
acquire a respiratory signal;
calculate a frequency power spectrum of the respiratory signal to generate a respiratory signal power spectrum;
calculate a frequency power spectrum for each of the plurality of deformation vectors to generate a plurality of deformation vector power spectrums; and sum the products of the respiratory signal power spectrum and the deformation vector power spectrums to generate the transformation effectiveness value.

20. A multi-modality imaging system comprising a first modality unit, a second modality unit, and a computer operationally coupled to the first and second modality units, wherein the computer is programmed to:
acquire a four-dimensional (4D) CT image data set;
acquire a four-dimensional (4D) PET image data set;
sort the CT and PET image data sets into separate field-of-view bins using a temporal gating system;
generate a plurality of deformation vectors using the sorted CT and PET image data sets; and
generate a transformation effectiveness value directly from the plurality of deformation vectors the transformation effectiveness value being representative of the effectiveness of the image transformation process.

21. A multi-modality imaging system in accordance with claim 20, wherein said computer is further programmed to:
automatically derive CT and PET bin-to-bin deformation vectors;
compare the CT and PET deformation vectors on a bin-by-bin basis; and
generate at least one of a global registration map and a local registration map based on the comparison.

22. A multi-modality imaging system in accordance with claim 20, wherein said computer is further programmed to:
automatically derive CT and PET bin-to-bin deformation vectors;
compare the CT and PET deformation vectors on a bin-by-bin basis;
generate at least one of a global registration map and a local registration map based on the comparison; and
generate at least one of a local registration, a global registration, and a combined local and global registration using at least one of the global motion registration map and a local motion registration map to generate the transformation effectiveness value.

23. A non-transitory computer readable medium encoded with a program programmed to instruct a computer to:
acquire a four-dimensional (4D) image data set;
sort the 4D image data set into separate field-of-view bins using a temporal gating system;
automatically generate a plurality of deformation vectors using the sorted 4D image data set; and
generate a transformation effectiveness value directly from the plurality of deformation vectors, the transformation effectiveness value being representative of the effectiveness of the image transformation process.

24. A non-transitory computer readable medium in accordance with claim 23, said computer readable medium is further programmed to instruct a computer to:
select the reference image from the 4D image data set; and
generate a motion deformation vector between the voxels in each of the n images and a respective voxel in the reference image to generate the plurality of motion deformation vectors.

25. A non-transitory computer readable medium in accordance with claim 23, said computer readable medium is further programmed to instruct a computer to:
generate a respiratory signal;
calculate a frequency power spectrum of the respiratory signal;
calculate a frequency power spectrum for each of the plurality of deformation vectors; and
compare the power spectrum of the respiratory signal to the power spectrum of the plurality of deformation vectors to generate the transformation effectiveness value.

26. A non-transitory computer readable medium in accordance with claim 23, said computer readable medium is further programmed to instruct a computer to:
generate a motion signal;
calculate a frequency power spectrum of the motion signal to generate a motion signal power spectrum;
calculate a frequency power spectrum for each of the plurality of deformation vectors to generate a plurality of deformation vector power spectrums; and
sum the products of the motion signal power spectrum and the deformation vector power spectrums to generate the transformation effectiveness value.

* * * * *